(12) United States Patent
Bazin et al.

(10) Patent No.: US 6,340,747 B1
(45) Date of Patent: Jan. 22, 2002

(54) FLUORESCENT CONJUGATES OF NUCLEOSIDES OR NUCLEOTIDES, PROCESS FOR THEIR PREPARATION AND THEIR USES

(75) Inventors: Hervé Bazin, Villeneuve les Avignon; Gérard Mathis, Bagnols sur Ceze, both of (FR)

(73) Assignee: CIS BIO International, Saclay (FR)

( * ) Notice: Subject to any disclaimer, the term of this patent is extended or adjusted under 35 U.S.C. 154(b) by 0 days.

(21) Appl. No.: 09/508,697

(22) PCT Filed: Oct. 2, 1998

(86) PCT No.: PCT/FR98/02111
§ 371 Date: Apr. 20, 2000
§ 102(e) Date: Apr. 20, 2000

(87) PCT Pub. No.: WO99/18114
PCT Pub. Date: Apr. 15, 1999

(30) Foreign Application Priority Data

Oct. 3, 1997 (FR) .............................. 97 12379

(51) Int. Cl.[7] .................. C07H 21/00; C12Q 1/68; C07D 267/02; C07F 5/00
(52) U.S. Cl. .................. 536/23.1; 536/22.1; 536/25.3; 536/25.32; 435/6; 540/549; 534/15
(58) Field of Search .................. 540/549; 534/15; 536/22.1, 23.1, 25.3, 25.32; 435/6

(56) References Cited

U.S. PATENT DOCUMENTS

| 5,220,012 A | 6/1993 | Mathis et al. | 540/459 |
| 5,457,185 A | 10/1995 | Lehn et al. | 534/15 |
| 5,512,493 A | 4/1996 | Mathis et al. | 436/537 |
| 5,527,684 A | 6/1996 | Mabile et al. | 435/7.1 |

FOREIGN PATENT DOCUMENTS

EP 0321353 * 6/1989

* cited by examiner

Primary Examiner—Jezia Riley
(74) Attorney, Agent, or Firm—Dennison, Scheiner, Schultz & Wakeman

(57) ABSTRACT

The invention relates to novel fluorescent conjugates of nucleosides or nucleotides which can be used especially for detecting, locating and/or isolating nucleic acids or molecules of biological or clinical interest which have a nucleoside structure or are capable of interacting with nucleic acids. The invention further relates to the polynucleotides comprising at least one fluorescent conjugate of a nucleotide.

22 Claims, 4 Drawing Sheets

K-4-dUTP

K-11-dUTP

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 1
ggcctgctga aaatgactga atat                                    24

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:PRIMER

<400> SEQUENCE: 2
tgttggatca tattcgtcca caaaatg                                 27

<210> SEQ ID NO 3
<211> LENGTH: 117
<212> TYPE: DNA
<213> ORGANISM: Artificial Sequence
<220> FEATURE:
<223> OTHER INFORMATION: Description of Artificial Sequence:PRIMER

<400> SEQUENCE: 3
ggcctgctga aaatgactga atataaactt gtggtagttg gagctggtgg cgtaggcaag    60
agtgccttga cgatacagct aattcagaat cattttgtgg acgaatatga tccaaca      117

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:PRIMER

<400> SEQUENCE: 4
gccttgacga tacagc                                             16

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence:PRIMER -continued

```
<400> SEQUENCE: 5
taatacgact cactataggg gtggatcata ttcgtccaca aaatg                45

<210> SEQ ID NO 6
<211> LENGTH: 132
<212> TYPE: DNA
<213> ORGANISM: Artificial Sequence
<220> FEATURE:
<223> OTHER INFORMATION: Description of Artificial Sequence:PRIMER

<400> SEQUENCE: 6
ctgctgaaaa tgactgaata taaacttgtg gtagttggag ctggtggcgt aggcaagagt    60
gccttgacga tacagctaat tcagaatcat tttgtggacg aatatgatcc acccctatag  120
tgagtcgtat ta                                                      132

<210> SEQ ID NO 7
<211> LENGTH: 115
<212> TYPE: RNA
<213> ORGANISM: Artificial Sequence
<220> FEATURE:
<223> OTHER INFORMATION: Description of Artificial Sequence:PRIMER

<400> SEQUENCE: 7
guggaucaua uucguccaca aaaugauucu gaauuagcug uaucgucaag gcacucuugc   60
cuacgccacc agcuccaacu accacaaguu uauauucagu cauuuucagc aggcc       115

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:PRIMER

<400> SEQUENCE: 8
gttggagctg gtggcgtagg                                               20
```

FLUORESCENT CONJUGATES OF NUCLEOSIDES OR NUCLEOTIDES, PROCESS FOR THEIR PREPARATION AND THEIR USES

This is a 371 of PCT/FR98/02111 filed on Oct. 2, 1998.

The invention relates to novel fluorescent conjugates of nucleosides or nucleotides which can be used especially for detecting, locating and/or isolating nucleic acids or molecules of biological or clinical interest which have a nucleoside structure or are capable of interacting with nucleic acids.

The following abbreviations will be used in the remainder of the description:
RNA: ribonucleic acid
DNA: deoxyribonucleic acid
A: adenosine
C: cytidine
G: guanosine
T: thymidine
U: uridine
I: inosine
suffix MP: monophosphate
suffix DP: diphosphate
suffix TP: triphosphate
prefix d: deoxy A reaction for the enzymatic synthesis of DNA employs an RNA or DNA template, an oligonucleotide primer whose sequence is complementary to a segment of the template, an appropriate enzyme, and the four deoxynucleotides dATP, dCTP, dGTP and dTTP (or dUTP). Various enzymes are known, such as *E. coli* DNA polymerase, T7 DNA polymerase, the Klenow fragment of DNA polymerase, Taq DNA polymerase and a reverse transcriptase, to which may be added terminal nucleotidyl transferase, which has the particular characteristic of not requiring a template. The synthesis of RNA is carried out in a similar manner except that the required primers and templates are different and ribonucleotides (ATP, CTP, GTP and UTP) are used in the presence of RNA polymerases.

Nucleotides or polynucleotides can be labeled radioactively ($^3$H, $^{32}$P, $^{14}$C, $^{35}$S or $^{125}$I).

The use of labeled molecules has the disadvantages conventionally associated with radioactive isotopes, namely the risks inherent in radioactivity as well as the limited storage and availability due to radioactive decay and radiolysis phenomena.

The chemical labeling of nucleotides or polynucleotides, which makes it possible to avoid these disadvantages, has been described in the literature. The biotin labeling of nucleotides derived from dUTP or UTP has been described in particular (Langer P. R., Waldrop A. A., Ward D. C., 1981, Proc. Natl. Acad. Sci. USA, 78, 6633–37). These are derivatives in which the biotin is bonded to the C-5 position of the pyrimidine ring by an alkylamine arm. These labeled nucleotides are incorporated in vitro into polynucleotides by the action of DNA or RNA polymerases (EP 0 063 879) and allow the calorimetric detection of nucleic acids by means of a dot-blot reaction (Leary J. J., Brigati D. J. and Ward D. D., 1983, Proc. Natl. Acad. Sci. USA, 80, 4045–49).

Other analogs of biotin-labeled nucleotides, based on derivatives of N-4-aminoalkyldeoxycytidine and N-6-aminoalkyldeoxyadenosine, are described in patent U.S. Pat. No. 4,828,979 and in Gebegehu G. G. et al., Nucleic Acids Res., 1987, 15, 4513–4534.

Derivatives of dUTP and of dATP substituted by biotin in the C-8 position, as well as the possibility of the C-7 substitution of a 7-deazapurine, are also described (EP 0 063 879).

The derivative bio-15-dGTP has also been described (Gilliam I. C. and Tener G. M., 1989, Nucleoside & Nucleotide, 8, 1453–62). Fluorescent derivatives such as fluorescein or rhodamine can be incorporated into a nucleic acid via a labeled nucleoside triphosphate (dATP, dUTP, dCTP) (WO 93 19206). A discussion about the position of substitutions on purines and pyrimidines and about the nature of the spacer arms which can be used to label dideoxynucleotides with fluorescein derivatives, although devoted to chain terminators for sequencing, gives an overview of the chemistry of labeled nucleotides (Confalone P. T., 1990, J. Heterocyclic Chem., 27, 31–46).

The combined use of nucleoside triphosphates labeled with different tracers (biotin-11-dUTP, dig-11-dUTP and FITC-11-dUTP) affords the simultaneous visualization of different sequences during a hybridization (REED T. et al., Proc. Natl. Acad. Sci. USA (1992), 89, 1388–1392).

The incorporation of fluorescein-labeled deoxynucleotides such as Fl-dUTP or Fl-dCTP is also effected by replacing only part of the natural nucleotide with the labeled compound: dCTP/Fl-dCTP≈2:1 (WO 93/19206). This same patent describes that, by choosing the enzyme and the experimental conditions, it is possible to replace the whole of a nucleotide with a labeled nucleotide.

The literature data show that the efficiency of incorporation of a tripbosphate conjugate is modified by coupling with a molecule such as biotin and to a lesser extent by the presence of the arm which allows the coupling.

For example, in a nick translation reaction in the presence of a DNA polymerase, the degrees of incorporation of various triphosphate analogs were compared with the natural nucleoside taken as a reference (100% incorporation) for the same reaction time (90 min) (Gebeyehu G. et al., Nucleic Acids Res., 1987, 15, 4525).

Molecules conjugated with nucleoside triphosphates (Goodchild, J. Bioconjugate Chem., 1990, p. 171; Kricka J., Non isotopic Blotting, and Sequencing, 1995, Academic Press, p. 47; Zhu Z. et al., Nucleic Acids Res., 1994, 3418–3422) are molecules of relatively small size (<800 Da) which are either neutral or negatively charged and have an essentially planar shape; consequently, their bulk is reduced but sufficient to disturb the enzymatic incorporation of the nucleoside triphosphate.

Novel conjugates of nucleosides or nucleotides have now been found which comprise:

a ribo- or deoxyribo-nucleoside or -nucleotide which is native, chemically modified or conjugated with one or more labeling molecules, in which at least one carbon atom of the ring, exocyclic nitrogen atom of the purine or pyrimidine ring or carbon atom of the pentofuranose ring may be involved in bonding with a fluorescent marker, and at least one fluorescent marker bonded to said atom(s) and consisting of a rare earth cryptate.

The invention may be better understood from the following detailed description, taken in conjunction with the accompanying drawings, in which.

Figure 1:
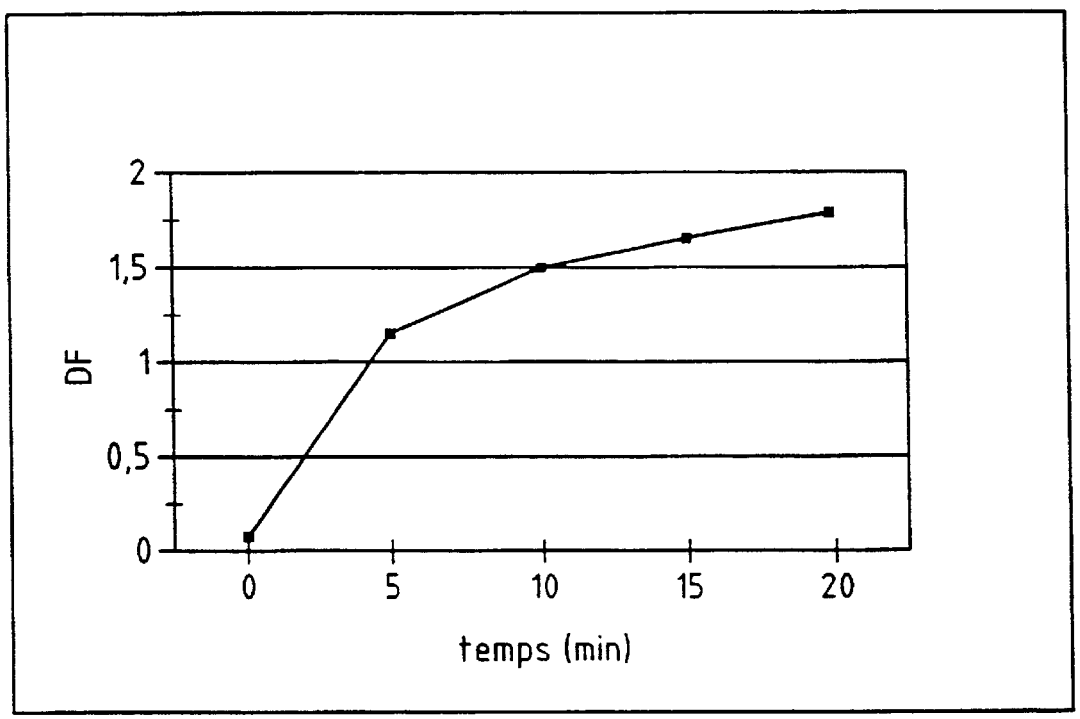
FIG. 1 illustrates a plot of the value of DF as a function of reaction time for incorporation of K-11-dUTP.

According to a preferred feature, said conjugates comprise:

a ribo- or deoxyribo-nucleoside or -nucleotide which is native, chemically modified or conjugated with one or more labeling molecules, in which at least one carbon atom of the ring or exocyclic nitrogen atom of the purine or pyrimidine ring may be involved in bonding with a fluorescent marker, and at least one fluorescent marker bonded to said atom(s) and consisting of a rare earth cryptate.

Said conjugates can be used in any applications of labeled nucleosides or nucleotides without their use presenting major disadvantages, and in particular they have a high capacity for incorporation into single-stranded or double-stranded DNA.

These properties are all the more surprising because rare earth cryptates are molecules of high molecular weight (greater than 1400 Da), possess a three-dimensional structure exhibiting more steric hindrance than a globally plane molecule, and are of an ionic nature due to the presence of the complexed ion, which gives them a positive charge.

Given these structural characteristics, the positive charges of a rare earth cryptate could be expected to interact strongly with the negative charges of the triphosphate group and to modify its reactivity as well as the fluorescent properties of the cryptate.

Also, as the activity of enzymes such as polymerases is sensitive to the presence and concentration of certain complexing ions or agents in the reaction medium, the conjugates according to the invention could be expected to cause a considerable decrease in the incorporation of the nucleotide triphosphates, and hence a low yield, especially during a polynucleotide synthesis.

Surprisingly, the results obtained using the conjugates according to the invention show that not only do rare earth cryptates not have an unfavorable influence in applications involving enzymatic reactions, but also they retain their intrinsic fluorescent properties.

Advantageously, it has also been found that the conjugates according to the invention have novel fluorescent characteristics and that, in particular, the emission lifetime of the complexed rare earth ion is significantly increased.

Said conjugates can therefore be used as fluorescent markers in any uses where a quantitative or qualitative detection is effected by measurement of the direct or indirect fluorescence.

According to a preferred feature, the invention relates to fluorescent conjugates of nucleotides comprising a ribonucleotide selected from AMP, ADP, ATP, GMP, GDP, GTP, CMP, CDP, CTP, UMP, UDP, UTP, TMP, TDP, TTP, 2Me-AMP, 2Me-ADP, 2Me-ATP, 1Me-GMP, 1Me-GDP, 1Me-GTP, 5Me-CMP, 5Me-CDP, 5Me-CTP, 5MeO-CMP, 5MeO-CDP, 5MeO-CTP, 7-deaza-ATP and 7-deaza-GTP, or, if appropriate, a deoxyribonucleotide selected from the deoxy- or dideoxyribonucleotides corresponding to these ribonucleotides, and in particular:

- 2'-deoxyuridine 5'-triphosphate or uridine 5'-triphosphate derivatives functionalized in the 5-position of the base (principally an aminoallyl or aminopropyne skeleton),
- 2'-deoxycytidine 5'-triphosphate or cytidine 5'-triphosphate derivatives functionalized in the 4- or 5-position of the base (principally an aminoallyl or aminopropyne skeleton in the case of the 5-position),
- 2'-deoxyadenosine 5'-triphosphate or adenosine 5'-triphosphate derivatives functionalized in the 6- or 8-position of the base,
- 2'-deoxyguanosine 5'-triphosphate or guanosine 5'-triphosphate derivatives functionalized in the 6- or 8-position of the base,
- 2'-deoxy-7-deazaadenosine 5'-triphosphate or 7-deazaadenosine 5'-triphosphate derivatives functionalized in the 7-position of the base, and
- 2'-deoxy-7-deazaguanosine 5'-triphosphate or 7-deazaguanosine 5'-triphosphate derivatives functionalized in the 7-position of the base.

The nucleotides which can be used for the purposes of the invention also include nucleotides chemically modified on the triphosphate part, particularly α-thiotriphosphate derivatives.

According to another feature, the invention relates to fluorescent conjugates of nucleosides in which the ribo- or deoxyribonucleoside is selected from A, G, C, U, T, the corresponding deoxy- or dideoxynucleosides and their chemically modified analogs, particularly 3'-azido-3'-deoxythymidine and its derivatives, and the 2',3'-dideoxy analogs of A, T, C, G, U and I.

The fluorescent marker consists of a rare earth cryptate preferably selected from terbium, europium, samarium or dysprosium cryptates.

In the remainder of the description, the term "cryptate" and the nomenclature of the macrocycles and polycycles which can be used are as defined by J. M. Lehn in Struct. Bonding (Berlin), 16, 1, 1973 and in Acc. Chem. Res., 11, 49 (1978).

According to a preferred feature, said rare earth cryptate consists of at least one rare earth salt complexed by a macropolycyclic compound of the formula

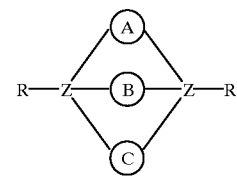

I in which Z is a tri- or tetravalent atom, R is nothing, hydrogen, the hydroxyl group, an amino group or a hydrocarbon radical, and the divalent radicals Ⓐ, Ⓑ and Ⓒ independently of one another are hydrocarbon chains which optionally contain one or more heteroatoms and are optionally interrupted by a heteromacrocycle, at least one of the radicals Ⓐ, Ⓑ and Ⓒ also containing at least one molecular moiety or essentially consisting of a molecular moiety, said molecular moiety possessing a greater triplet energy than that of the emission level of the complexed rare earth ion.

Said rare earth cryptate is preferably a cryptate of formula (I) above in which the molecular moiety is selected from phenanthroline, anthracene, benzene, naphthalene, bi- and terphenyl, azobenzene, azopyridine, pyridine, bipyridines, bis-quinolines and the compounds of the following formulae:

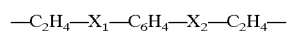

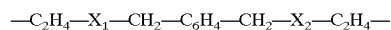

in which $X_1$ and $X_2$, which can be identical or different, are oxygen, nitrogen or sulfur, and

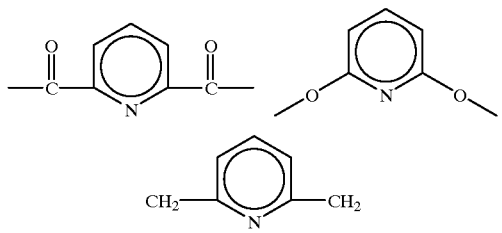

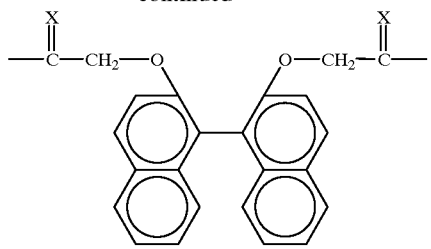

in which X is oxygen or hydrogen.

According to an advantageous feature, the fluorescent marker is a rare earth cryptate consisting of the terbium or europium ion complexed by one of the following macrocyclic compounds:

[2.2.phenanthroline]; [2.2.phenanthroline amide]; [2.2.anthracene]; [2.2.anthracene amide]; [2.2.biisoquinoline]; [2.2.biphenyl-bis-pyridine]; [2.2.bipyridine]; [2.2.bipyridine amide]; and tris-bipyridine, tris-phenanthroline, phenanthroline-bisbipyridine, biisoquinoline-bis-bipyridine and bis-bipyridine diphenylbipyridine macropolycycles.

One particularly advantageous marker is the europium cryptate Eu tris-bipyridine.

Such compounds are described for example in patent EP 180 492.

It is also possible to use macropolycyclic cryptate compounds which complex rare earth ions and in which the molecular moiety is selected from bipyrazines, bipyrimidines and nitrogen heterocycles containing N-oxide groups.

Macropolycyclic compounds with bipyrazine units are described in F. Bodar-Houillon et al., New J. Chem., 1996, 20, 1041–1045.

Macropolycyclic compounds with bipyrimidine units are described in J. M. Lehn et al., Helv. Chim. Acta, 1992, 75, 1221.

Macropolycyclic compounds comprising nitrogen heterocycles containing N-oxide groups are described in J. M. Lehn et al., Helv. Chim. Acta, 1991, 74, 572.

The rare earth cryptate used as the fluorescent marker can also consist of at least one rare earth salt complexed by a macropolycyclic compound of formula II or III below:

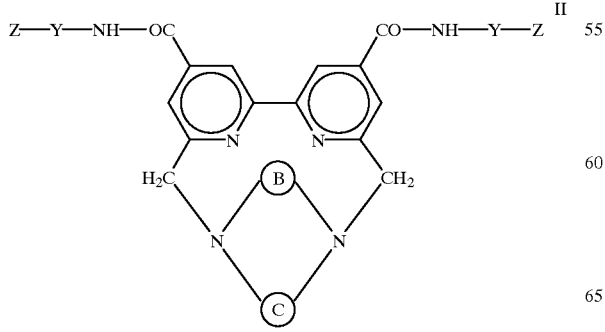

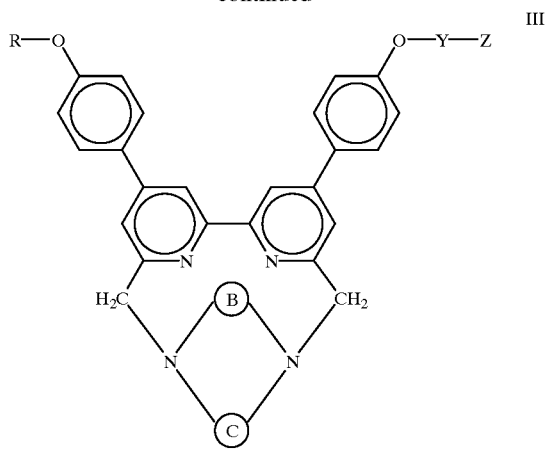

in which:
the ring of the formula

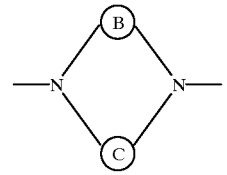

is one of the following rings:

1)

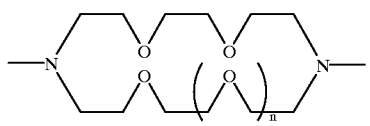

n = 0 or 1
[N₂O₄] macrocycle or (22) ring
[N₂O₃] macrocycle or (21) ring

2)

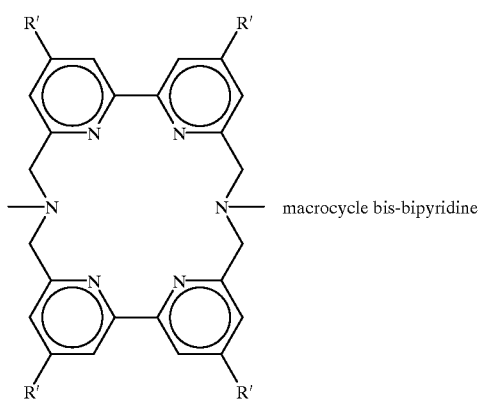

macrocycle bis-bipyridine

Y is a group or spacer arm consisting of a divalent organic radical selected from linear or branched $C_1$ to $C_{20}$ alkylene groups optionally containing one or more double bonds and/or optionally containing one or more heteroatoms such as oxygen, nitrogen, sulfur or phosphorus, or one or more carbamoyl or carboxamido groups, from $C_5$ to $C_8$ cycloalkylene groups or from $C_6$ to $C_{14}$ arylene groups, said alkylene, cycloalkylene or arylene groups optionally being substituted by alkyl, aryl or sulfonate groups;

Z is a functional group capable of bonding covalently with a biological substance;

R is a methyl group or the group -Y-Z; and

R' is hydrogen or a group —COOR", in which R" is a $C_1$ to $C_{10}$ alkyl group, preferably the methyl, ethyl or tert-butyl group, or R' is a group —CO—NH—Y—Z.

Such compounds are described for example in patent EP 321 353.

Within the conjugates according to the invention, said fluorescent marker can be bonded to the ribo- or deoxyribo-nucleoside or -nucleotide either directly or via a spacer arm.

"Direct bonding" is understood as meaning the bonding of the fluorescent marker to a functional group previously introduced onto or generated on one or more atoms of the base or of the pentofuranose unit of the ribo- or deoxyribo-nucleoside or -nucleotide.

In the present description, functional group is understood as meaning any function carried by the nucleoside or nucleotide part or introduced onto this part by any method known to those skilled in the art, and capable of bonding covalently, either directly or after activation, with a function present on the cryptate or on the spacer arm carried by the cryptate. Such functional groups are especially the $NH_2$, COOH, CHO, OH or SH functions, as well as functions capable of producing covalent bonds by substitution (halides, sulfonates, epoxide) or by addition (double bonds of the maleimide type). These functions are generally carried by a hydrocarbon chain, which is itself joined to the nucleoside or nucleotide part.

Methods of introducing these functional groups are described especially in C. Kessler, Nonisotopic probing, Blotting and Sequencing, 2nd edition, L. J. Kricka (1995), published by Academic Press Ltd, London, pp. 66–72.

This spacer arm consists for example of a divalent organic radical selected from linear or branched $C_1$–$C_{20}$ alkylene groups optionally containing one or more double bonds or triple bonds and/or optionally containing one or more heteroatoms such as oxygen, nitrogen, sulfur or phosphorus, or one or more carbamoyl or carboxamido groups; $C_5$–$C_8$ cycloalkylene groups; and $C_6$–$C_{14}$ arylene groups, said alkylene, cycloalkylene or arylene groups optionally being substituted by alkyl, aryl or sulfonate groups.

In particular, it can be selected from the following groups:

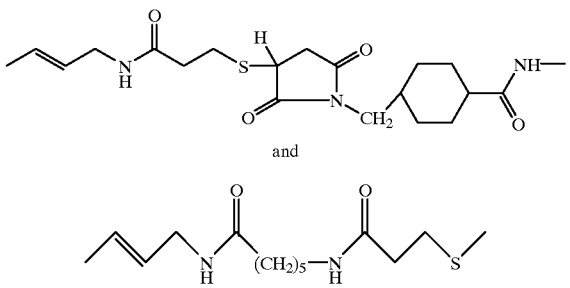

According to a preferred feature, the conjugate according to the invention comprises deoxyuridine as a deoxyribonucleotide, the europium cryptate Eu tris-bipyridine as a fluorescent marker and a 3-aminoallyl group as a spacer arm.

According to another feature, the invention further relates to a process for the preparation of the conjugates described above.

Said preparative process is characterized in that a ribo- or deoxyribonucleoside or -nucleotide which is native, chemically modified or conjugated with one or more labeling molecules, in which at least one carbon atom of the ring, exocyclic nitrogen atom of the purine or pyrimidine ring or carbon atom of the pentofuranose unit may be involved in bonding with a fluorescent marker, is reacted with at least one fluorescent marker bonded to said atom(s) and consisting of a rare earth cryptate, and in that the resulting conjugate is isolated.

The ribo- or deoxyribo-nucleosides or -nucleotides and the fluorescent markers which can be used in this preparative process are as described above.

The conjugates according to the invention which comprise a ribo- or deoxyribonucleotide are particularly suitable for all applications which require a qualitative or quantitative measurement during the synthesis or use of polynucleotides.

According to one of its features, the invention further relates to the polynucleotides comprising at least one fluorescent conjugate of a ribo- or deoxyribonucleotide, as described above, as a constituent nucleotide.

Advantageously, the polynucleotides obtained by the incorporation of conjugates according to the invention can comprise a number of conjugates greater than 1 and hence a number of fluorescent markers greater than 1.

By using the conjugates according to the invention, it is thus possible to effect the multiple labeling of polynucleotides by an enzymatic method. This technique affords labeled polynucleotides more easily and assures a better reproducibility than when using the conventional techniques of fluorescent labeling by a chemical method. In particular, it avoids the separation steps which are necessary for removing the unreacted polynucleotides and/or unreacted functionalized fluorescent markers from the medium.

It will be noted that it bifunctionalized cryptates are used, conjugation takes place on only one arm, which always allows the incorporation of the conjugate within the framework of a polynucleotide synthesis.

The conjugates according to the invention which comprise a ribo- or deoxyribonucleotide can be used for detecting and/or locating compounds containing at least one nucleic acid sequence.

Among these uses, the following may be mentioned without implying a limitation:

the detection and/or location of specific DNA sequences, for example for mapping chromosomes or detecting a mutation; and the synthesis of probes which can be used in biomedical research or for establishing a clinical diagnosis.

They can also be used in a method of measuring the enzymatic activity of an enzyme involved in a nucleic acid synthesis reaction, for example a DNA or RNA polymerase, reverse transcriptase, transferase or ligase activity, where the fluorescence emitted directly or indirectly by said conjugate is measured, said fluorescence emission being correlated with the degree of incorporation of said conjugate into the synthesized nucleic acid polynucleotide.

The conjugates according to the invention can also be used for measuring the enzymatic activity of an enzyme with a nucleic acid substrate, for example a phosphodiesterase, DNAse or RNAse activity, the fluorescence emitted directly or indirectly by said conjugate being correlated either with said activity or with the inhibition of said activity.

They can also be used for measuring an enzymatic activity which modifies the structure of a nucleic acid, such as a helicase or integrase activity, or an activity which modifies the topology of a nucleic acid, such as a topoisomerase activity.

The conjugates according to the invention can also be used as markers, for example for the preparation of a compound comprising a nucleic acid into which said conjugate is incorporated for the purpose of detection.

The fluorescence emitted by the conjugates according to the invention can be either "direct", i.e. the luminous signal is emitted by the conjugate after excitation at a given wavelength, or "indirect", i.e. the emission of the luminous signal is induced by a non-radiative energy transfer between the excited conjugate, or "donor compound", and another fluorescent molecule, or "acceptor compound".

In this particular case, the following conditions are fulfilled:

on the one hand, the fluorescent acceptor compound possesses an absorption spectrum which at least partially overlaps the emission spectrum of the donor and has a high molar absorbance in this overlap zone, and an emission spectrum over a wavelength range in which the donor has a weak intrinsic emission;

on the other hand, the acceptor and the donor are situated near one another, the orientation of their transition dipoles being approximately parallel.

The principle of the technique of non-radiative energy transfer is described especially in G. Mathis et al., Clin. Chem., 1993, 39, 1953–1959.

The invention is illustrated by the Examples below, in which some concentrations are given in absorption units (AU) at a given wavelength (expressed in nm) per unit volume (expressed in ml) and are expressed by the same number as the optical density of the solution in question.

EXAMPLE 1

Synthesis of Deoxyuridine Labeled With the Cryptate Europium Tris-bipyridine (Conjugate K-11-dUTP)

In this conjugate the number 11 indicates the total number of atoms in the spacer arm and in the functional group joining the cryptate structure to the nucleotide (the bonding in this case takes place in the 5-position of the pyrimidine).

The nucleoside triphosphate used is 5-[N-(6-aminocaproyl)-3-aminoallyl]-2'-deoxyuridine 5'-triphosphate] (AH-dUTP), which is prepared by reacting N-hydroxysuccinimide trifluoroacetamidocaproate (M. S. Urdea et al., Nucleic Acids Res., 1988, 4937) with 5-(3-aminoalkyl)-2'-deoxyuridine 5'-triphosphate, which in turn is prepared by a literature process (Langer et al., Proc. Natl. Acad. Sci. USA (1981), 78, 6633–6637), and then carrying out an ammoniacal deprotection (3% aqueous $NH_4OH$, 45 min at 60° C.). The compound is purified on DEAE-Sepharose® (Pharmacia) under a linear triethylammonium hydrogencarbonate gradient (0.1 M to 0.3 M).

1) Method A

68 μl of a solution of AH-dUTP containing 6 μmol/ml (i.e. 0.4 μmol) are diluted with 250 μl of 0.1 M triethylammonium hydrogencarbonate (TEAB), pH 7.8, and 320 μl of a solution of N-hydroxysuccinimide cryptate (4 mg/ml in acetonitrile), prepared as below, are added. The cryptate europium [(bis-bpy)-(bpy-diester)] described in Example 4, section A, of patent application EP 0 321 353 is hydrolyzed with NaOH and the diacid cryptate obtained is purified on an RP-18 HPLC column (gradient of acetonitrile in 1% aqueous trifluoroacetic acid). The resulting cryptate, europium [(bis-bpy)-(bpy-diacid)] (4 mg), is dissolved in 0.5 ml of anhydrous acetonitrile, and 1 mg of N-hydroxysuccinimide is added, followed by a solution of 1.9 mg of dicyclohexylcarbodiimide dissolved in 0.5 ml of acetonitrile. After a reaction time of 16 h, the precipitate of dicyclohexylurea is filtered off and the solution of N-hydroxysuccinimide cryptate is used directly for coupling.

After stirring for 45 min, 15 μl of 1 M TEAB, pH 8.5, are added and the mixture is then injected onto a Superdex 30® HR 10/30 column (Pharmacia), which is eluted with 0.05 M TEAB, pH 7, containing 10% of acetonitrile (flow rate 1 ml/min).

The compound of Rt≡16.4 min is collected and this fraction, called fraction 1, is then concentrated under vacuum (speed-vac) to a volume of 350 μl and contains 8 $AU_{304\,nm}$. With an estimated $\epsilon_{304}$ of ≡35,000, it is estimated that the concentration of K-dUTP is about 0.72 mM.

An aliquot (90 μl) of this fraction 1 is injected onto the same column, which is eluted with 25 mM triethylammonium acetate buffer, pH 7, containing 5% of acetonitrile. The fraction corresponding to the only peak in the chromatogram is collected (16 min<Rt<19 min) and concentrated under vacuum (speed-vac) to give 150 μl of a solution of K-dUTP, called fraction 2, containing 1.95 $AU_{304\,nm}$.

The compound is analyzed by mass spectrometry (positive mode electrospray):

$(M-2H)^+=1431$ $(M-2H+CH_3COOH)^+=1491$

The UV spectrum in water has a maximum at 241 nm characteristic of the nucleoside part of the molecule ($\lambda_{max}=$ 289 nm, $\epsilon=7100$; $\lambda_{max}=240$ nm, $\epsilon=10,700$), and a maximum at 304 nm, which is near the $\lambda_{max}$ of 305 nm ($\epsilon=30,000$) characteristic of the europium cryptate. A ratio $A_{304}/A_{241}$ of ≡0.83 is observed, which is compatible with the proposed structure.

2) Method B 0.08 μmol of a solution of AH-dUTP is dissolved in 80 μl of 0.1 M borate buffer, pH 8.6, and 90 μl of a solution of N-hydroxysuccinimide cryptate (4 mg/ml), prepared as described above in method A, are added.

After 60 min at 20° C., 5 μl of 1 M TEAB, pH 8.5, and 45 μl of $H_2O$ are added. The whole of the reaction mixture is injected onto a Superdex peptide HR 10/30 column (Pharmacia), which is eluted with 0.05 M TEAB, pH 7, containing 10% of acetonitrile (flow rate 1 ml/min).

The peak of Rt≡16.1 min, which has a maximum at 304 nm and a ratio $A_{304}/A_{241}$ of ≡0.79, is collected to give about 0.03 μmol of the compound K-11-dUTP.

Figure 2:
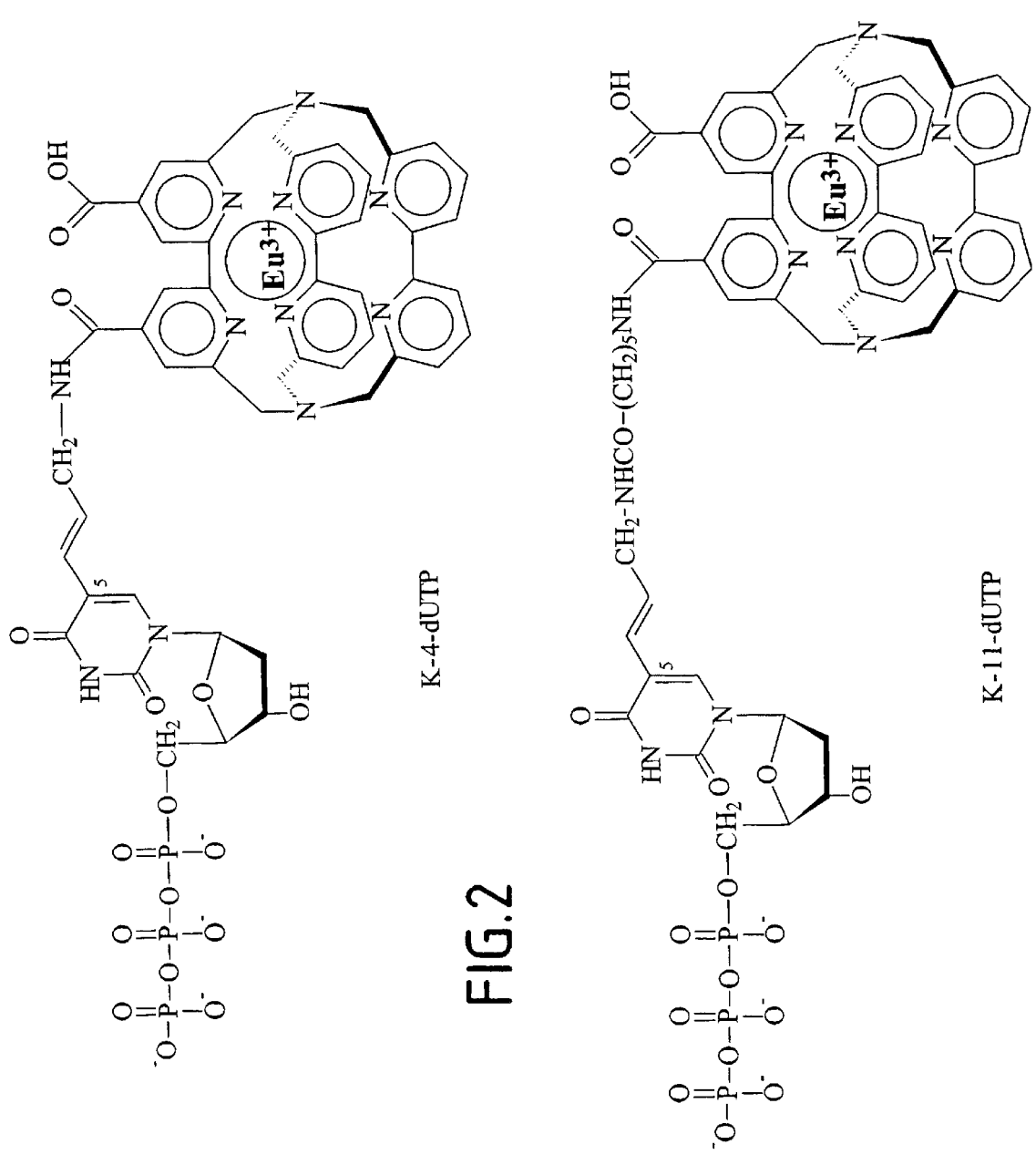
FIG. 2 illustrates the chemical formulae of K-4-dUTP and K-11-dUTP.

The formula of the conjugate K-11-dUTP is given in FIG. 2.

EXAMPLE 2

Purification of the Conjugate K-11-dUTP By Ion Exchange

The column used is a C10/20 column (Pharmacia Biotech., Uppsala, S) packed with DEAE Sepharose® Fast Flow (Pharmacia) equilibrated in 10 mM TEAB buffer containing 10% of methanol. A solution of K-11-dUTP, also containing non-conjugated, functionalized europium tris-bipyridine cryptate, is deposited and the column is eluted (8 ml/min) with 40 ml of buffer A (10 mM TEAB containing 10% of methanol). 4 ml fractions are collected and the fluorescence of the eluted fractions is measured ($\lambda_{excitation}=$ 337 nm, $\lambda_{emission}=620$ nm). The non-conjugated cryptate is eluted in fractions 4 and 5, i.e. shortly after the dead volume of the column.

Elution is continued (8 ml/min) under a linear gradient from 10 mM TEAB, 10% methanol (100 ml) to 200 mM TEAB, 10% methanol (100 ml) and 5 ml fractions are collected. It is observed that the fluorescence (620 nm) is concentrated in tubes 43 to 44, indicating that the K-11-dUTP is eluted at a concentration of ≡0.16 mM TEAB. The fractions containing the K-11-dUTP are combined and concentrated.

EXAMPLE 3

Incorporation of the Conjugate K-11-dUTP During the Copying of a Single-stranded DNA By Means of a Polymerase (Analysis By PAGE and Autoradiography)

The template DNA is obtained by the PCR (Polymerase Chain Reaction) amplification of a fragment of the k-ras gene (exon I) bounded by the following primers:

k-ras EX1 sense S primer $^5$'d(GGC CTG CTG AAA ATG ACT GAA TAT)$_3$' stock solution containing 3 $AU_{260}$/ml, i.e. about $1.2 \cdot 10^{-5}$ M k-ras EX1 antisense AS primer $5'd$(TGT TGG ATC ATA TTC GTC CAC AAA ATG)$_3$, stock solution containing 3 $AU_{260}$/ml, i.e. about $1.2 \cdot 10^{-5}$ M The AS primer used here for the PCR below is biotinylated at its 5' end. A biotinylated double-stranded DNA is synthesized by PCR using the following protocol:

PCR medium 25 µl of BUAM (CIS bio international) 10×
8 µl of antisense-bio primer
8 µl of sense primer
10 µl of Taq polymerase (1.25 U/ml)
10 µl of dNTP (four natural dNTPs, 5 mM each)
100 µl of human placenta DNA (Sigma), 0.01 µg/µl
89 µl of milli-Q water The PCR medium is divided up into 5 microtubes (5×50 µl) and the tubes are placed in a thermocycler and subjected to 31 PCR cycles according to the protocol of Example 5.

The double-stranded DNA produced by the PCR (equivalent to 25 pmol of biotin primer) is incubated in the presence of 300 µg of Dynabeads-streptavidin M-280 (Dynal, N).

After washing, the single-stranded DNA (SS DNA) is eluted with 0.1 N sodium hydroxide solution, after which the supernatant is decanted and neutralized (dilute HCl) and then concentrated to a residual volume of 60 µl.

An AS primer (non-biotinylated) as defined above, labeled with $^{32}P$, as described in J. Sambrook et al., Molecular cloning, a laboratory manual, 1989, is used for the remainder of the manipulation.

Media for the copying reaction are prepared using the following:

K-11-dUTP fraction 1 (Rt=16.4 min) obtained in Example 1, diluted to 0.25 mM dTTP, 0.25 mM mixture of 3 deoxynucleotide triphosphates (dATP, dCTP and dGTP), 0.625 mM each Taq DNA polymerase, 1.25 U/µl Taq (BUAM) 10×buffer (Cis bio international)

AS primer (3 $AU_{260}$/ml) and $^{32}P$-labeled AS primer (0.06 $AU_{260}$/ml)

A parallel control reaction is carried out in which the K-11-dUTP is replaced with 0.6 µl of dTTP (0.25 mM) so that the concentration of dTTP in the medium is the same as for the other three triphosphates.

|  | Volume (µl) |
|---|---|
| BUAM 10X | 1 |
| Taq DNA polymerase | 0.2 |
| $^{32}$P S primer | 2 |
| S primer | 0.35 |
| 3 triphosphates | 0.5 |
| K-11-dUTP | 0.6 |
| dTTP | 0.6 |
| SS DNA | 5 |

Polyacrylamide gel electrophoresis (PAGE) is used to verify that the reaction in the presence of the conjugate K-11-dUTP produces a band corresponding to a copy of the DNA over the whole of its length and having a mobility close to that of the band obtained for the control reaction where only the four natural nucleotides are introduced. Furthermore, the electrophoresis profile shows no reading discontinuities in either case.

The same manipulation was carried out using variable ratios dTTP/K-11-dUTP, inter alia with 0.3 µl of K-11-dUTP and 0.9 µl of dTTP (dTTP/K-11-dUTP=3).

The copying reaction was also carried out in the presence of DNA polymerase I, Klenow fragment (37° C., 45 min) to give substantially the same results.

These results show that the conjugate dUTP/europium tris-bipyridine cryptate is indeed incorporated by a polymerase (Taq polymerase or Klenow fragment) during the copying of the single-stranded DNA.

EXAMPLE 4

Incorporation of the Conjugate K-11-dUTP During the Copying of a Single-stranded DNA By Means of a Polymerase (Verification By Non-radiative Energy Transfer and Time Resolved Fluorescence Measurement)

The single-stranded DNA described in Example 3 is used.

A microtube for carrying out the copying reaction (50 µl) is prepared which contains:

K-11-dUTP: 0.25 mM fraction 1 (Rt=16.4 min), obtained in Example 1 dTTP: 0.25 mM mixture of 3 deoxynucleotide triphosphates: dATP, dCTP and dGTP, 0.625 mM each biotinylated AS primer (cf. Example 3): 3 $AU_{260}$/ml Taq DNA polymerase: 1.25 U/µl Taq buffer: BUAM 10×

|  | Volume (µl) |
|---|---|
| BUAM 10X | 5 |
| Taq polymerase | 1 |
| Biotinylated primer | 1.75 |
| Mix of 3 dNTps | 2.5 |
| K-11-dUTP | 3 |
| dTTP | 3 |
| SS DNA | 30 |
| Milli-Q water | 3.75 |

The tubes are heated for 2 min at 90° C. (denaturation) and then incubated at 70° C. in a thermocycler. Samples (9 µl) are taken at 0, 5, 10, 15 and 20 min. The aliquots are placed in tubes containing 2 µl of 0.5 M EDTA solution, pH 8.

This gives the equivalent of 12.5 pmol of biotinylated primers per 50 µl of reaction mixture, i.e. 2.5 pmol per 10 µl. There are also 150 pmol of K-11-dUTP per 10 µl.

The samples are diluted at a rate of 8 µl in 200 µl of buffer L (0.1 M phosphate, pH 7, 0.15 M NaCl, 0.4 M KF and 0.1% BSA) and then diluted to 1/10 in the same buffer.

20 µl (equivalent to $2 \cdot 10^{-14}$ mol of biotin) of samples (diluted as described above) are pipetted into the "test" wells of a microplate (PACKARD HTRF-96 96-well flat bottom black low fluorescence microplate). 30 µl of the conjugate SA-XL$_{665}$ (conjugate of streptavidin and chemically modified allophycocyanin, CIS bio international) diluted in buffer L (final concentration $2 \cdot 10^{-8}$ M) are added to each "test" well ($6.5 \cdot 10^{-13}$ mol of SA, i.e. 30 equivalents based on biotin), followed by 250 µl of buffer L.

20 µl of diluted samples are pipetted into the "blank" wells, to which 280 µl of buffer L are added.

After incubation (15 min at 37° C.), the fluorescence is read immediately at 620 nm and 665 nm on a Discovery instrument (PACKARD HTRF microplate analyzer).

The ratios of the fluorescence intensities, Re=E665/E620 for each test and Ro=B665/B620 for each blank, are calculated and then the value of DF=(Re−Ro)/Ro, expressed as a percentage, is calculated. The results are reported in Table 1 below.

In the Table, as in the remaining Examples, the fluorescence measurements at 620 nm or 665 nm are expressed in arbitrary fluorescence units which depend on the instrument used for the measurement.

TABLE 1

| Time (min) | E665 | E620 | Re = E665/E620 | B665 | B620 | Ro = B665/B620 | DF |
|---|---|---|---|---|---|---|---|
| 0 | 1590 | 35,770 | 0.044 | 1615 | 39,423 | 0.041 | 8% |
| 5 | 3670 | 42,016 | 0.087 | 1718 | 42,961 | 0.040 | 118% |
| 10 | 4077 | 40,448 | 0.100 | 1713 | 42,234 | 0.040 | 149% |
| 15 | 4185 | 38,670 | 0.108 | 1633 | 40,089 | 0.040 | 166% |
| 20 | 5357 | 49,403 | 0.108 | 1993 | 51,777 | 0.038 | 182% |

A plot of the value of DF as a function of the reaction time gives the typical profile of the kinetics of nucleotide incorporation during enzymatic copying (FIG. 1).

EXAMPLE 5

Incorporation of the Conjugate K-11-dUTP During a PCR (Verification by Non-radiative Energy Transfer and Time Resolved Fluorescence Measurement)

1) PCR

A region of exon 1 of the k-ras gene bounded by the S and AS primers described in Example 3 is amplified.

This generates an amplification product with a length of 117 bp and the following sequence (sense strand):

5'd(GGC CTG CTG AAA $^1$ATG ACT GAA TAT AAA CTT GTG GTA GTT $^{10}$GGA GCT GGT GGC GTA GGC AAG AGT GCC TTG $^{20}$ACG ATA CAGCTA ATT CAG AAT CAT TTT GTG $^{30}$GAC GAA TAT GAT CCA ACA)$_3$.

A probe (56% G+C) is selected from the central part of the amplified sequence (underlined above). A biotin is introduced at its 5' end with the aid of an N-4-aminohexyl-dC arm (A. Roget et al., Nucleic Acids Res., 1989, 17, 7643–7651): CP probe: biotin-dC. GCC TTG ACG ATA CAG C.

Stock solution containing 0.3 $AU_{260}$/ml, i.e. about $1.7.10^{-6}$ M. 48 μl of the K-11-dUTP fraction (13 $AU_{304}$/ml), repurified from a TEAAc buffer (cf. Example 1, method A), are diluted with 32 μl of milli-Q water, i.e. a final concentration of K-11-dUTP of about 0.2 mM.

A mixture of the following 4 natural deoxynucleotide triphosphates is used: 5 mM dATP, 5 mM dCTP, 5 mM dGTP and 3.5 mM dTTP.

The following PCR stock mixture is prepared:

25 μl of BUAM buffer (CIS bio international) 10×

10 μl of dNTP

8 μl of S primer

8 μl of AS primer

10 μl of Taq DNA polymerase (i.e. 12.5 U)

9 μl of milli-Q water

In PCR microtubes, the PCR media are prepared according to the following Table using 0.01 μg/μl of human placenta DNA (Sigma).

| | T- | T+ | K1- | K1+ | K2- | K2+ |
|---|---|---|---|---|---|---|
| Mixture (μl) | 7 | 7 | 7 | 7 | 7 | 7 |
| dTTP (μl) | 1.5 | 1.5 | 0 | 0 | 0 | 0 |
| K-11-dUTP (μl) | 0 | 0 | 1 | 1 | 2 | 2 |
| DNA (μl) | 0 | 10 | 0 | 10 | 0 | 10 |
| Milli-Q water (μl) | 16.5 | 6.5 | 17 | 7 | 16 | 6 |
| [K-11-dUTP] (μM) | 0 | 0 | 8 | 8 | 16 | 16 |
| [dTTP] (μM) | 200 | 200 | 140 | 140 | 140 | 140 |
| [K-11-dUTP]/[dTTP] | — | — | 0.06 | 0.06 | 0.12 | 0.12 |

The PCR is carried out using the following protocol:

1. 5 min/95° C., 2.1 1 min/94° C. (denaturation)

2.2 1 min/60° C. (circularization)

2.3 1 min/70° C. (elongation) (31 cycles)

3.1 8 min/70° C. (final elongation)

The reactions are monitored by agarose gel electrophoresis. Only tubes containing DNA (T+, K1+ and K2+) give a band of the expected length (by comparison with the 124 bp band of Boehringer marker VIII).

2) Time Resolved Measurement of the Energy Transfer

The principle of the measurement consists in hybridizing the biotinylated CP probe on the amplified DNA fragment and then bringing the hybrid into contact with the conjugate $SA-XL_{665}$ (defined in Example 4). The incorporation of bases labeled with europium cryptate (donor) results in a non-radiative energy transfer to $XL_{665}$ (acceptor) when the donor is excited at about 337 nm.

In this case the acceptor emits fluorescence at 665 nm with a long lifetime, enabling this signal to be differentiated from the inherent fluorescence of the acceptor, which has a short lifetime.

Time resolved fluorescence measurements are made at 620 nm and 665 nm in the presence of the acceptor ("test" E620 and E665) and in the absence of the acceptor ("blank" B620 and B665) and then the ratios Re=E665/E620 and Ro=B665/B620 are calculated. The value of DF=(Re−Ro)/Ro, expressed as a percentage, is then calculated. An increase in the value of DF shows the presence of an energy transfer and hence the incorporation of the cryptate into the amplified DNA.

The media K1−, K1+, K2− and K2+ originating from the PCRs are used. 2 μl of each PCR medium are deposited in microtubes, 10 μl of CP probe (0.03 $AU_{260}$/ml) and 13 μl of BUAM buffer (2×) are added and the sealed tubes are heated for 10 min at 94° C. and then for 20 min at 50° C. with the aid of a thermocycler. 5 μl of hybridization medium are diluted in 200 μl of buffer L, and 40 μl of this dilution are pipetted into the "test" wells of a microtiter plate and 40 μl into the "blank" wells (Packard HTRF 96-well flat bottom microplate).

40 μl of $3.10^{-8}$ M $SA-XL_{665}$ (CIS bio international) and 200 μl of buffer L are added to the "test" wells. 240 μl of buffer L are added to the "blank" wells.

After incubation for 15 min at 37° C., the fluorescence is measured immediately on a Discovery instrument (Packard).

The results are reported in Table 2 below.

TABLE 2

| Tube | E665 | E620 | Re | B665 | B620 | Ro | DF |
|---|---|---|---|---|---|---|---|
| K1− | 889 | 16,053 | 0.0554 | 847 | 16,825 | 0.0503 | 10% |
| K1+ | 2406 | 28,392 | 0.0847 | 1366 | 32,494 | 0.0420 | 102% |
| K2− | 1320 | 29,015 | 0.0455 | 1273 | 31,452 | 0.0405 | 12% |
| K2+ | 3304 | 36,615 | 0.0902 | 1491 | 36,278 | 0.0411 | 120% |

The results show that the conjugate K-11-dUTP is incorporated during a PCR. Furthermore, the presence of cryptate molecules bonded to the amplified DNA can be demonstrated by hybridization with a probe specific for this amplified DNA and disclosed by a non-radiative energy transfer between the cryptate and an acceptor bonded to the hybridized probe.

EXAMPLE 6
Synthesis of Deoxyuridine Labeled With the Cryptate Europium Tris-bipyridine (K-4-dUTP)

In this compound the number 4 indicates the total number of atoms in the arm joining the cryptate structure to the nucleotide (the bonding in this case takes place in the 5-position of the pyrimidine).

The nucleoside triphosphate used is 5-(3-aminoallyl)-2'-deoxyuridine 5'-triphosphate (AA-dUTP), which is prepared by a literature process (Langer et al., Proc. Natl. Acad. Sci. USA (1981), 78, 6633–6637). The compound is purified on DEAE-Sepharose® (Pharmacia) under a triethylammonium hydrogencarbonate gradient (10 mM to 300 mM).

60 μl of a solution of AA-dUTP containing 5.4 μmol/ml (i.e. 0.3 μmol) are diluted with 240 μl of 0.1 M triethylammonium hydrogencarbonate (TEAB), pH 7.8, and 300 μl of a solution of activated cryptate [TBP-(Eu$^{3+}$)] containing 4 mg/ml in acetonitrile, i.e. 0.85 μmol (about 3 equivalents), are added. The activated cryptate [TBP-(Eu$^{3+}$)] is prepared for immediate use as described in Example 1, method A.

After shaking for 35 min, 15 μl of 1 M TEAB, pH 8.5, are added and the mixture is concentrated to half and then injected onto a Superdex 30® HR 10/30 column (Pharmacia), which is eluted with 25 mM TEAB, pH 9, containing 10% of acetonitrile (flow rate 1 ml/min).

The compound of Rt≡16.3 min is collected; this fraction, called fraction 1, is concentrated under vacuum (speed-vac) to a volume of 200 μl and then injected onto the same column, which is eluted with 25 mM triethylammonium acetate buffer, pH 7, containing 5% of acetonitrile. The fraction corresponding to the only peak in the chromatogram is collected (16 min<Rt<19 min) and concentrated under vacuum (speed-vac) to give 260 μl of a solution of K-4-dUTP, called fraction 2, containing 6.0 AU$_{303}$. With an estimated $\epsilon_{303}$ of ≡35,000, it is estimated that the concentration of K-4-dUTP is about 0.65 mM.

The compound is analyzed by mass spectrometry (negative mode electrospray):

(M–4H)=1315.5 (calculated for 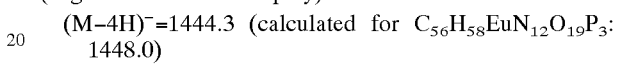: 1319)

The UV spectrum in water has a maximum at 243 nm characteristic of the nucleoside ($\lambda_{max}$=289 nm, $\epsilon$=7100; $\lambda_{max}$=240 nm, $\epsilon$=10,700), and a maximum at 303 nm, which is near the $\lambda_{max}$ of 305 nm ($\epsilon$=27,000) characteristic of the europium cryptate. A ratio A$_{303}$/A$_{240}$ of ≡0.82 is observed, which is compatible with the proposed structure.

The formula of the conjugate K-4-dUTP is given in FIG. 2.

EXAMPLE 7
Synthesis of Uridine Labeled With the Cryptate Europium Tris-bipyridine (K-11-UTP)

In this compound the number 11 indicates the total number of atoms in the spacer arm joining the cryptate structure to the nucleotide (the bonding in this case takes place in the 5-position of the pyrimidine).

The nucleoside triphosphate used is 6-aminocaproyl-[5-(3-aminoallyl)uridine 5'-triphosphate] (AH-UTP), which is prepared as indicated in Example 1. The compound is purified on DEAE-Sepharose® (Pharmacia) under a linear triethylammonium hydrogencarbonate gradient (25 mM to 300 mM).

400 μl of a solution of AH-dUTP containing 1.1 μmol/ml (i.e. 0.44 μmol) in 0.1 M triethylammonium hydrogencarbonate (TEAB), pH 7.8, are used and 360 μl of a solution of activated cryptate [TBP-(Eu$^{3+}$)] (3 mg/ml in acetonitrile) are added. The activated cryptate [TBP-(Eu$^{3+}$)] is prepared for immediate use as described in Example 1, method A.

After stirring for 45 min, 40 μl of 1 M TEAB, pH 8.5, are added and the mixture is then injected onto a Superdex peptide 30® HR 10/30 column (Pharmacia), which is eluted with 50 mM TEAB, pH 7, containing 10% of acetonitrile (flow rate 1 ml/min).

The compound of Rt≡15.4 min is collected; this fraction, called fraction 1, is concentrated under vacuum (speed-vac) to a volume of 200 μl, which contains ≡10 AU$_{304 \, nm}$. With an estimated $\epsilon_{304}$ of ≡35,000, it is estimated that the concentration of K-11-UTP is about 0.3 mM.

This fraction 1 is injected onto the same column, which is eluted with 25 mM triethylammonium acetate buffer, pH 7, containing 5% of acetonitrile. The fraction corresponding to the only peak in the chromatogram is collected (Rt≡16.5 min) and concentrated under vacuum (speed-vac) to give 202 μl of a solution of K-11-UTP, called fraction 2, containing 7.5 AU$_{304 \, nm}$.

The compound is analyzed by mass spectrometry (negative mode electrospray):

(M–4H)=1444.3 (calculated for C$_{56}$H$_{58}$EuN$_{12}$O$_{19}$P$_3$: 1448.0)

The UV spectrum in water has a maximum at 241 nm characteristic of the nucleoside ($\lambda_{max}$=289 nm, $\epsilon$=7100; $\lambda_{max}$=240 nm, $\epsilon$=10,700), and a maximum at 303 nm, which is near the $\lambda_{max}$ of 305 nm ($\epsilon$=27,000) characteristic of the europium cryptate. A ratio A$_{304}$/A$_{241}$ of ≡0.80 is observed, which is compatible with the proposed structure.

The compound is analyzed by FPLC (mono-Q column, Pharmacia). Buffer A: 20 mM sodium acetate, pH 5.2, containing 10% of acetonitrile. Buffer B: 20 mM sodium acetate, pH 5.0, and 1 M LiCl containing 10% of acetonitrile. Linear gradient from 0 to 30% B in 25 min. Flow rate 1 ml/min. The K-11-UTP has an Rt of 10.7 min.

Figure 3:
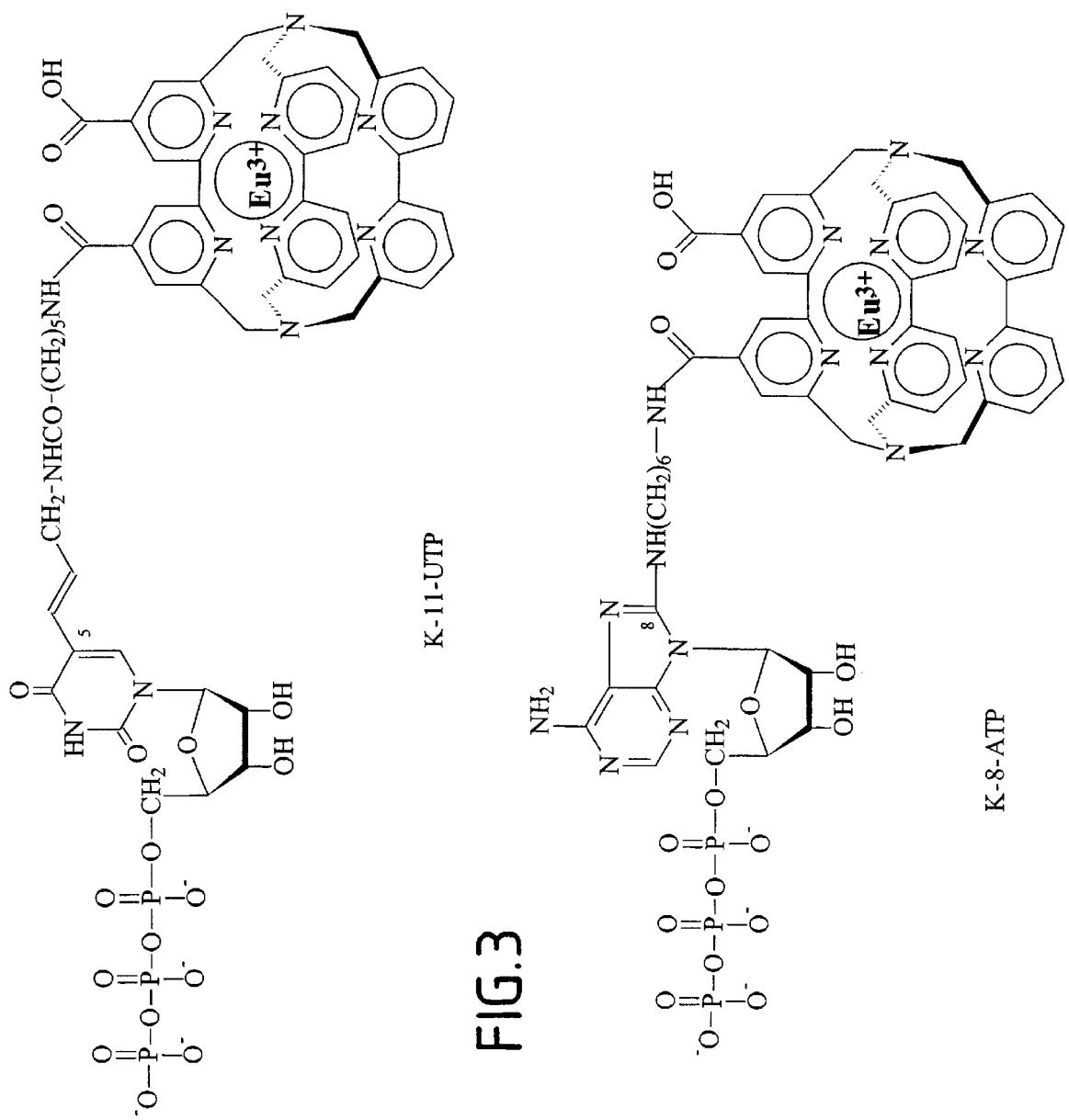
FIG. 3 illustrates the chemical formulae of K-11-UTP and K-9-ATP.

The formula of the conjugate K-11-UTP is given in FIG. 3.

EXAMPLE 8
Comparative Measurements of the Lifetimes of the Conjugates of dUTP and UTP With the Cryptate Europium Tris-bipyridine and of the Cryptate Alone The reference cryptate used is the cryptate europium [(bis-bpy)(bpy-di(amidoethyleneamine))] described in Example 4 of patent application EP 0 321 353 (hereafter called KNH$_2$).

A stock solution of KNH$_2$ in water is prepared and its concentration is determined by measurement of the optical density at 306 nm, taking a value of ≡30,000 for $\epsilon_{306}$. The stock solution (6.7×10$^{-4}$ M) is diluted to 1/100 in 0.1 M Tris-HCl buffer, pH 9; 100 μl of this intermediate dilution are then diluted in 600 μl of the same buffer. In parallel, a stock solution of K-11-dUTP, K-4-dUTP and K-11-UTP (prepared according to Example 1, method A, and Examples 6 and 7 respectively) is prepared in water, whose concentration is estimated as 3×10$^{-5}$ M by measurement of the optical density at 304 nm ($\epsilon_{304}$≡35,000). Each stock solution is diluted at a rate of 50 μl in 1 ml of 0.1 M Tris-HCl buffer, pH 7.4, or in 0.1 M Tris-HCl buffer, pH 9.

The values of the emission lifetime of the europium (τ in ms) are measured using an LS50 time resolved spectrofluorimeter (Perkin-Elmer) and Helma 5 mm×5 mm cells.

The results are reported in Table 3 below:

TABLE 3

| Compound | Lifetime τ (ms) in 0.1 M Tris buffer, pH 7.4 | Lifetime τ (ms) in 0.1 M Tris buffer, pH 9 |
| --- | --- | --- |
| K-11-dUTP | 0.587 | 0.596 |
| K-4-dUTP | 0.621 | 0.651 |

TABLE 3-continued

| Compound | Lifetime τ (ms) in 0.1 M Tris buffer, pH 7.4 | Lifetime τ (ms) in 0.1 M Tris buffer, pH 9 |
|---|---|---|
| K-11-UTP | 0.636 | 0.640 |
| KNH$_2$ (reference) | 0.368 | 0.265 |

These results show that the coupling of the nucleotide with the cryptate molecule results in an increase in the lifetime of the europium and in new fluorescent characteristics for the cryptate/nucleotide conjugate relative to the reference cryptate.

EXAMPLE 9

Incorporation of K-11-dUTP During the Elongation of an Oligonucleotide By Means of Terminal Nucleotidyl Transferase (Verification By Non-radiative Energy Transfer and Time Resolved Fluorescence Measurement)

A microtube for carrying out the elongation reaction is prepared using:

25 μl of 0.2 M Tris-acetate buffer, pH 7.2

4 μl of 25 mM aqueous cobalt chloride solution

5 μl of a 2.4 μM solution of an oligonucleotide (composition A$_2$C$_3$G$_7$T$_3$ biotinylated at the 5' end) in H$_2$O 2 μl of K-11-dUTP (fraction 2, prepared according to Example 7) at a concentration 0.04 mM 8 μl of 0.04 mM dTTP 5 μl of water 1 μl of terminal deoxynucleotidyl transferase (TnT, EC 2.7.7.31) (Sigma, 35 U/μl)

2 μl of the reaction mixture are taken and added to 4 μl of 60 mM EDTA (to obtain a control at t$_0$=0 min) and the remainder is incubated at 37° C. for a kinetic study. After reaction times of 5, 10, 20, 40, 60 and 80 min at 37° C., 2 μl of the reaction mixture are taken and added to 4 μl of 60 mM EDTA in order to stop the reaction. This gives fractions t$_5$, t$_{10}$ etc. These fractions t$_0$, t$_5$, t$_{10}$ are diluted with 250 μl of buffer L (0.1 M phosphate, pH 7, 0.15 M NaCl, 0.4 M KF and 0.1% BSA).

50 μl (equivalent to 2.3.10$^{-12}$ mol of biotin) of samples diluted as described above are pipetted into the "test" wells (called E$_0$, E$_5$, E$_{10}$ etc.) of a microplate (PACKARD HTRF-96 96-well flat bottom black low fluorescence microplate). 50 μl of the conjugate SA-XL$_{665}$ (CIS bio international) diluted in buffer L (1.5.10$^{-8}$ M) are added to each "test" well, followed by 150 μl of buffer L.

A "blank" is prepared from a reaction mixture described above in which the enzyme has been replaced with 1 μl of water. 2 μl of this mixture are taken and subjected to the treatments and dilutions described above. 50 μl of this diluted sample are pipetted into the "blank" wells, to which 50 μl of the conjugate SA-XL$_{665}$ and 150 μl of buffer L are added.

After incubation (15 min at 37° C.), the fluorescence is read at 620 nm and 665 nm on a DISCOVERY instrument (PACKARD HTRF microplate analyzer).

The ratios of the fluorescence intensities, Re=E665/E620 for each test and Ro=B665/B620 for each blank, are calculated and then the value of DF=(Re−Ro)/Ro, expressed as a percentage, is calculated. The results are reported in Table 4 below.

TABLE 4

| Time (min) | 0 | 5 | 10 | 20 | 40 | 60 | 80 |
|---|---|---|---|---|---|---|---|
| F665 | 602 | 1585 | 2186 | 3610 | 5347 | 8204 | 5542 |
| F620 | 9559 | 10,757 | 9921 | 11,023 | 10,754 | 10,589 | 8971 |
| Re = F665/F620 | 0.063 | 0.147 | 0.22 | 0.327 | 0.497 | 0.77 | 0.618 |
| DF | 0 | 129 | 242 | 409 | 673 | 1104 | 865 |

The blank has a ratio B$_{665}$/B$_{620}$ of 0.064. For t$_0$ a ratio E$_{665}$/E$_{620}$ of 0.063 is observed, the transfer being DF=100×(Re−Ro)/Ro=100(0.063−0.064)/0.064, i.e. virtually zero. By calculating DF for each time in this way, it is observed that the energy transfer expressed as the value of DF increases over time, showing that the K-11-dUTP is incorporated into the oligonucleotide chain by the terminal nucleotidyl transferase.

EXAMPLE 10

Photophysical Properties of an Oligonucleotide into Which Cryptate Molecules are Incorporated A reaction to incorporate K-11-dUTP by means of TnT is carried out according to Example 9 with a 3-fold increase in all the amounts. DF is measured as a function of time in order to verify that the incorporation of K-11-dUTP follows the same kinetics. After a reaction time of 80 min, the reaction is stopped with 12 μl of 400 mM EDTA solution. 105 μl of the reaction mixture are taken and deposited on an NAP5 column (Pharmacia) equilibrated in 10 mM phosphate buffer, pH 7.4.

The oligonucleotide is eluted with 600 μl of buffer. This fraction, called "fraction 1" (exclusion volume), is analyzed as follows: 50 μl of fraction 1 are deposited in the wells of a microplate and 200 μl of buffer L are added to give the "cryptate blank". 50 μl of fraction 1, 50 μl of the conjugate SA-XL$_{665}$ (CIS biointernational) (1.5.10$^{-8}$ M in buffer L) and 150 μl of buffer L are deposited in the adjacent "test" wells. The fluorescence is measured at 620 nm and 665 nm on a DISCOVERY instrument (PACKARD HTRF microplate analyzer).

The lifetime τ is calculated from the slope of the line obtained by plotting log E$_{620}$=f(t).

The emission lifetime is measured at 620 nm for the labeled oligonucleotide contained in fraction 1 (10 mM phosphate buffer, pH 7.4) using a KRYPTOR time resolved fluorimeter (CIS bio international) with excitation at 337 nm. This gives a lifetime τ of 866 μs. This lifetime is longer than that of the conjugate K-11-dUTP (τ=681 μs), measured simultaneously under the same conditions.

By comparing the fluorescence of fraction Fl (which corresponds to the cryptate molecules incorporated into the oligonucleotide chain) with the fluorescence of standard solutions containing a known concentration of cryptate, it is possible to estimate that fraction Fl contains about 5.10$^{-11}$ mol of cryptate, given that the estimated amount of oligonucleotide in fraction Fl is 2.10$^{-11}$, it is observed that a number n=5.10$^{-11}$/2.10$^{-11}$=2.5 labeled cryptate-labeled nucleotides have been incorporated on average per oligonucleotide chain.

In this compound the number 8 indicates the total number of atoms in the spacer arm joining the cryptate structure to the nucleotide (the bonding in this case takes place in the 8-position of the purine).

The nucleoside triphosphate used is [8-(6-aminohexyl) adenosine 5'-triphosphate] (AH-ATP, Sigma). A solution of 0.1 μmol of AH-ATP in 100 μl of 0.1 M triethylammonium hydrogencarbonate (TEAB), pH 8, is used and 100 μl of a solution of activated cryptate [TBP-(Eu$^{3+}$)] (4 mg/ml in acetonitrile) are added. The activated cryptate [TBP-(Eu$^{3+}$)] (NHS/DCC in acetonitrile) is prepared for immediate use as described in Example 1, method A.

After shaking for 35 min, 5 µl of 1 M TEAB are added and the mixture is concentrated to half and then injected onto a Superdex 30® HR 10/30 column (Pharmacia), which is eluted with 50 mM TEAB, pH 8, containing 10% of acetonitrile (flow rate 1 ml/min).

The compound of Rt≡16.7 min is collected; this fraction, called fraction 1, is concentrated under vacuum (speed-vac) to a volume of 200 µl and then injected onto the same column, which is eluted with 25 mM triethylammonium acetate buffer, pH 7, containing 5% of acetonitrile. The fraction corresponding to the only peak in the chromatogram is collected (Rt=17.2 min) and concentrated under vacuum (speed-vac).

The UV spectrum in water has a maximum at 245 nm, a maximum at 283 nm, which is near the $\lambda_{max}$ characteristic of the nucleoside ($\lambda_{max}$=279, $\epsilon$=21,000), and a maximum at 303 nm, which is near the $\lambda_{max}$ of 305 nm ($\epsilon$=27,000) characteristic of the europium cryptate. A ratio $A_{305}/A_{280}$ of ≡1 is observed, which is compatible with the proposed structure.

The formula of the conjugate K-8-ATP is given in FIG. 3.

EXAMPLE 12

Incorporation of a Conjugate of UTP With the Cryptate Europium Tris-bipyridine (K-11-UTP) During an In Vitro Transcription Reaction (Verification By Non-radiative Energy Transfer and Time Resolved Fluorescence Measurement)

This Example concerns the simultaneous incorporation of K-11-UTP and bio-14-CTP (CTP/biotin conjugate) into one and the same RNA molecule by in vitro transcription.

1/Transcription

The transcription reaction of a double-stranded DNA containing a promoter (plasmid DNA pSTP18 and pSTP19 containing the T7 promoter and linearized by EcoRI) to RNA is carried out with the aid of an SP6/T7 transcription kit (Boehringer-Mannheim). The transcript obtained has a length of 1035 bases.

In addition to the ribonucleotides at a final concentration of 0.5 mM, the transcription medium contains 0.2% of K-11-UTP and 30% of bio-14-CTP, which will be incorporated randomly along the chain.

The K-11-UTP, fraction 2, described in Example 7 is diluted in water to give a concentration of 20 µM.

The solution of bio-14-CTP is prepared by diluting a commercial 10 mM solution of biotin-14-CTP (Gibco-BRL/Life Technologies) in water.

The transcription medium is prepared in PCR microtubes (0.5 ml) according to the Table below: bio-14-CTP (CTP/biotin conjugate) into one and the same RNA molecule by in vitro transcription.

1/Transcription

The transcription reaction of a double-stranded DNA containing a promoter (plasmid DNA pSTP18 and pSTP19 containing the T7 promoter and linearized by EcoRI) to RNA is carried out with the aid of an SP6/T7 transcription kit (Boehringer-Mannheim). The transcript obtained has a length of 1035 bases.

In addition to the ribonucleotides at a final concentration of 0.5 mM, the transcription medium contains 0.2% of K-11-UTP and 30% of bio-14-CTP, which will be incorporated randomly along the chain.

The K-11-UTP, fraction 2, described in Example 7 is diluted in water to give a concentration of 20 µM.

The solution of bio-14-CTP is prepared by diluting a commercial 10 mM solution of biotin-14-CTP (Gibco-BRL/Life Technologies) in water.

The transcription medium is prepared in PCR microtubes (0.5 ml) according to the Table below:

| | Volume | Final concentration | Labeled rNTP/ labeled rNTP + natural rNTP |
|---|---|---|---|
| Transcription buffer (10X) | 2 µl | | |
| Plasmid DNA (T7) (0.5 µg/µl) | 2 µl | | |
| ATP (5 mM) | 2 µl | 0.5 mM | |
| GTP (5 mM) | 2 µl | 0.5 mM | |
| UTP (5 mM) | 2 µl | 0.5 mM | |
| K-11-UTP (20 µM) | 2 µl | 2 µM | 0.4% |
| CTP (3.5 mM) | 2 µl | 0.35 mM | |
| Bio-14-CTP (1.5 mM) | 2 µl | 0.15 mM | 30% |
| RNAse inhibitor (20 U/µl) | 1 µl | | |
| H$_2$O | 1 µl | | |
| T7 RNA polymerase | 2 µl | | |
| Total volume | 20 µl | | |

After addition of the enzyme, 2 µl of the reaction medium are taken and immediately diluted with 38 µl of 50 mM EDTA solution, pH 8. This solution is then diluted by taking 19 µl and diluting it with 114 µl of buffer L. This solution will be used as a background control at $t_0$=0 min.

The reaction mixture is placed in a thermocycler at 37° C. After given reaction times (60 min, 90 min and 120 min), 2 µl of the reaction mixture are taken and diluted, as previously, with 38 µl of 50 mM EDTA, pH 8. These solutions are then diluted by taking 19 µl and diluting it with 114 µl of buffer L.

50 µl of each diluted solution, corresponding to the times 0 min, 60 min, 90 min and 120 min, are deposited in the wells of a black microplate (Packard HTRF 96-well flat bottom microplate).

50 µl of a solution of SA-XL$_{665}$ (CIS bio international) at a concentration of 6.25.10$^{-7}$ M in buffer L are added, followed by 100 µl of buffer L.

2/ Time Resolved Measurement of the Energy Transfer

After incubation (15 min at room temperature), the fluorescence is measured at 620 nm and 665 nm on a DISCOVERY instrument (Packard).

For each reaction time considered, the energy transfer is evaluated by calculating the ratio Re=F665/F620. The ratio Ro=F665/F620 for the time $t_0$ makes it possible to evaluate the background level. The same measurement made on a dilution of 2 µl of a transcription reaction mixture in which the enzyme has been replaced with an equivalent volume of water gives the same background level.

The energy transfer is calculated by the formula DF=(Re−Ro)/Ro for each time. The results are reported in Table 5 below.

TABLE 5

| Time (min) | F665 | F620 | Re = F665/F620 | DF = (Re − Ro)/Ro (%) |
|---|---|---|---|---|
| 0 | 2108 | 14,672 | 0.143 | 0 |
| 60 | 6329 | 18,755 | 0.337 | 135 |
| 90 | 6672 | 17,026 | 0.392 | 174 |
| 120 | 7386 | 18,179 | 0.406 | 184 |

It is observed that the value of DF increases, representing an increase in the energy transfer due to the incorporation of K-11-UTP and bio-CTP into the transcribed RNA.

The transcription reaction described above is monitored by electrophoresis on agarose gel (3%).

A large band is observed, showing the integrity of the RNA fragment produced. This band is characterized by an identical migration to that of the band produced from a transcription performed on the natural rNTPs alone.

Figure 4:
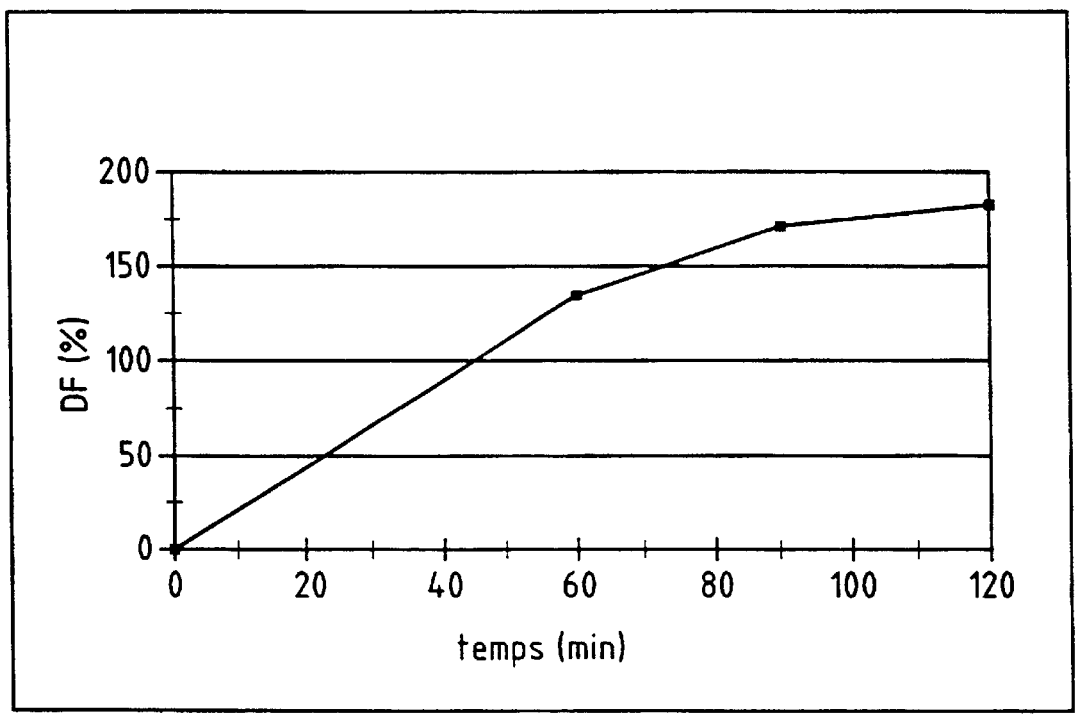
FIG. 4 illustrates a plot of the value of DF as a function of reaction time for incorporation of K-11-UTP.

The curve of the values of DF as a function of reaction time, given in FIG. 4, shows the typical profile of the kinetics of nucleotide incorporation during an enzymatic transcription. These results show that the conjugate K-11-UTP is incorporated efficiently by an RNA polymerase.

EXAMPLE 13

Incorporation of a Conjugate K-11-dUTP During an In Vitro Transcription Reaction (Verification By Non-radiative Energy Transfer and Time Resolved Fluorescence Measurement After Hybridization With an Acceptor Probe)

The transcription reaction of a double-stranded DNA to RNA is carried out with the aid of a transcription kit (Gibco BRL). The double-stranded DNA containing the T7 promoter is itself obtained by a PCR carried out with a pair of primers, one of which contains the sequence of the promoter of T7 RNA polymerase (EC 2.7.7.6).

The transcript obtained has a theoretical length of 115 bases.

The general principle of transcription by an RNA polymerase is described in p. 5.58 and 5.59 of "Molecular Cloning, A Laboratory Manual", 2nd edition, J. Sambrook, E. F. Fritsch and T. Maniatis, CSH Press 1989.

It is also possible to use another RNA polymerase, such as SP6 or T3 RNA polymerase, in which case the sequence of the PCR primer in question will be modified in order to incorporate the specific promoter of the RNA polymerase considered.

The incorporation of a promoter is described in §13.5 and §23.2 of "PCR: Clinical Diagnostics and Research", A. Rolfs et al., Springer-Verlag (1992), and in D. Y. Kwoth et al., Proc. Natl. Acad. Sci. USA (1989), 86, 1173–1177.

1/Preparation of the Double-stranded DNA Containing the Promoter of RNA Polymerase The protocol used is analogous to that described in Example 5 except that only deoxynucleotides are used to generate a primary PCR product of 117 bp.

A second PCR (secondary PCR) is carried out using 2 µl of a 1/100 dilution of the product of the primary PCR as the target DNA (DNA). For this secondary PCR the k-ras EX1 antisense primer is replaced with a primer, called T7-AS, of the following sequence:

5'd(TAA TAC GAC TCA CTA TAG GGG TGG ATC ATA TTC GTC CAC AAA ATG)$_3$.

The italicized part of this sequence corresponds to the sequence of the promoter of T7 RNA polymerase.

The k-ras EX1 sense primer has the following sequence:

5'd(CTG.CTG.AAA.ATG.ACT.GAA.TAT)$_3$.

The double-stranded DNA obtained after this secondary PCR has a theoretical length of 132 bp and the following sequence (sense strand):

5'd(CTG.CTG.AAA.ATG.ACT.GAA.TAT.AAA.CTT.GTG.GTA.
GTT.GGA.GCT.GGT.GGC.GTA.GGC.AAG.AGT.GCC.TTG
.ACG.ATA.CAG.CTA. ATT.CAG.AAT.CAT.TTT.GTG.GAC-
.GAA.TAT.GAT.CCA.CCC.CTA.TAG. TGA.GTC.GTA.TTA)$_3$.

The italicized part represents the T7 sequence (sense strand) and the underlined part represents the sequence corresponding to the probe during the hybridization step.

Transcription will produce the following RNA sequence (sequence homologous to the antisense strand of the transcribed DNA fragment), in which the underlined part corresponds to the sequence recognized by the biotinylated probe:

5'pppG.UGG.AUC.AUA.UUC.GUC.CA-
C.AAA.AUG.AUU.CUG.AAU. UAG.CUG.UAU.CGU-
.CAA.GGC.ACU.CUU.G
CC.UAC.GCC.ACC.AGC.UCC.AAC.UAC.CAC.AAG.U
UU.AUA.UUC.AGU.CAU.UUU.CAG.CAG.GCC$_3$.

The RAS12N probe used is biotinylated at the 5' end and has the following sequence:

2/Transcription

In addition to the natural ribonucleotides at a final concentration of 0.5 mM, the transcription medium contains 2% of K-11-UTP, which will be incorporated randomly along the RNA chain.

The K-11-UTP, fraction 2, described in Example 7 is diluted in water to give a concentration of 100 µM.

The transcription medium is prepared in PCR microtubes (0.5 ml) according to the Table below:

|  | Volume | Final concentration | K-11-UTP/ (K-11-UTP + UTP) |
|---|---|---|---|
| Transcription buffer(5X) | 10 µl |  |  |
| Positive PCR DNA(T7) (0.5 µg/µl) | 25 µl |  |  |
| DTT, 0.1M | 2 µl |  |  |
| Mix of rNTPs (5 mM each) | 5 µl | 0.5 mM |  |
| K-11-UTP (100 µM) | 5 µl | 10 µM | 2% |
| RNAse inhibitor(20 U/µl) | 2 µl |  |  |
| H$_2$O | 0.5 µl |  |  |
| T7 RNA polymerase(50 U/µl) | 0.5 µl |  |  |
| Total volume | 50 µl |  |  |

The reaction mixture is placed in a thermocycler at 40° C. for 120 min and the reaction is then stopped with 4 µl of 0.2 M EDTA, pH 8.

2 µl of the reaction medium are placed in a PCR microtube and diluted with 10 µl of the RAS12N probe (0.03 AU$_{260}$/ml in H$_2$O) and 13 µl of hybridization buffer (100 mM phosphate buffer, pH 7.4, 0.1% BSA, 1 M NaCl) are then added. The mixture is heated for 10 min at 70° C. and then hybridized for 20 min at 45° C. in a thermocycler.

5.5 µl of the above hybridization medium are diluted in buffer L (qsp 200 µl) to give the diluted hybridization medium HT$_{pos}$.

A blank is prepared by performing a transcription according to the above protocol except that the positive PCR DNA is replaced with an equivalent volume of PCR medium originating from a negative PCR, which does not contain the target DNA.

The negative transcription medium (2 µl) is stopped, a hybridization is then carried out as described above and the mixture is diluted in buffer L to give the diluted hybridization medium HT$_{neg}$.

3/ Time Resolved Measurement of the Energy Transfer

The incorporation of the cryptate into the RNA chain is demonstrated by hybridization with a probe complementary to the RNA sequence, this probe being labeled with the conjugate SA-XL$_{665}$ (CIS bio international) via the pair streptavidin/biotin.

50 μl of the HT$_{pos}$ medium and 50 μl of the conjugate SA-XL$_{665}$ (CIS bio international) diluted to $1.5.10^{-10}$ M in buffer L are deposited in the wells of a black microplate (Packard HTRF 96-well flat bottom microplate) and 100 μl of buffer L are then added. These wells will enable the energy transfer to be measured by calculating Re=E665/E620 as detailed in Example 5.

50 μl of the HT$_{neg}$ medium are deposited in the adjacent wells and 50 μl of the conjugate SA-XL$_{665}$ and 100 μl of buffer L are added as described above. These wells serve as a reference for evaluating the background by calculating Ro.

The fluorescence is measured at 620 nm and 665 nm on a DISCOVERY instrument (Packard).

The energy transfer is calculated by means of the formula DF=(Re−Ro)/Ro for each time. The results are reported in Table 6 below.

TABLE 6

| Medium | E665 | E620 | Re = E665/E620 | DF (%) |
|---|---|---|---|---|
| HT$_{neg}$ | 738 | 17,900 | 0.041 | |
| HT$_{neg}$ | 1714 | 15,010 | 0.114 | 178 |

A transfer of 178% is observed in the case where the transcription is performed in the presence of the target DNA.

---

What is claimed is:

1. A fluorescent conjugate of a nucleoside or nucleotide, comprising:

a ribo- or deoxyribo-nucleoside or -nucleotide which is native, chemically modified or conjugated with one or more labeling molecules, in which either:
 (a) at least one carbon atom of the ring or exocyclic nitrogen atom of the purine or pyrimidine ring or of the carbon atom of the pentofuranose unit is able to bond with a fluorescent marker; or
 (b) at least one carbon atom of the ring or exocyclic nitrogen atom of the purine or pyrimidine ring is able to bond with a fluorescent marker; and at least one fluorescent marker consisting of a rare earth cryptate bonded to said atom(s).

2. A conjugate according to claim 1, wherein the ribo- or deoxyribonucleotide is selected from the group consisting of:

2'-deoxyuridine 5'-triphosphate or uridine 5'-triphosphate derivatives functionalized in the 5-position of the base;

2'-deoxycytidine 5'-triphosphate or cytidine 5'-triphosphate derivatives functionalized in the 4- or 5-position of the base;

2'-deoxyadenosine 5'-triphosphate or adenosine 5'-triphosphate derivatives functionalized in the 6- or 8-position of the base;

2'-deoxyguanosine 5'-triphosphate or guanosine 5'-triphosphate derivatives functionalized in the 6- or 8-position of the base;

2'-deoxy-7-deazaadenosine 5'-triphosphate or 7-deazaadenosine 5'-triphosphate derivatives functionalized in the 7-position of the base; and 2'-deoxy-7-deazaguanosine 5'-triphosphate or 7-deazaguanosine 5'-triphosphate derivatives functionalized in the 7-position of the base.

3. Conjugate according to claim 1, characterized in that it is a fluorescent conjugate of a nucleotide comprising a ribonucleotide selected from AMP, ADP, ATP, GMP, GDP, GTP, CMP, CDP, CTP, UMP, UDP, UTP, TMP, TDP, TTP, 2Me-AMP, 2Me-ADP, 2Me-ATP, 1Me-GMP, 1Me-GDP, 1Me-GTP, 5Me-CMP, 5Me-CDP, 5Me-CTP, 5MeO-CMP, 5MeO-CDP, 5MeO-CTP, 7-deaza-ATP and 7-deaza-GTP, or a deoxyribonucleotide selected from the deoxy- or dideoxyribonucleotides corresponding to these ribonucleotides.

4. A conjugate according to claim 1, which is a fluorescent conjugate of a nucleoside in which the ribo- or deoxyribo-nucleoside is selected from the group consisting of A, G, C, U, T, the corresponding deoxy- or dideoxynucleosides and their chemically modified analogs.

5. A conjugate according to claim 1, wherein the deoxyribonucleoside or deoxribonucleotide is selected from the group consisting of 3'-azido-3'-deoxythymidine, derivatives of 3'-azido-3'-deoxythymidine and the 2',3'-dideoxy analogs of A, T, C, G, U and I.

6. A conjugate according to claim 1, wherein the fluorescent marker is bonded to a functional group introduced onto or generated on the base or on the pentofuranose unit of the ribo- or deoxyribo-nucleoside or -nucleotide, either directly or via a spacer arm.

7. A conjugate according to claim 1, wherein the fluorescent marker is selected from the group consisting of a terbium, europium, samarium and dysprosium cryptate.

8. A conjugate according to claim 1, wherein the fluorescent marker is a rare earth cryptate consisting of at least one rare earth salt completed by a macropolycyclic compound of the formula

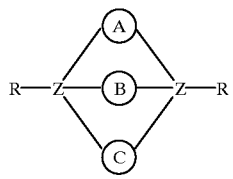

I in which Z is a tri- or tetravalent atom, R is nothing, hydrogen, the hydroxyl group, an amino group or a hydrocarbon radical, and the divalent radicals (A), (B) and (C) independently of one another are hydrocarbon chains which optionally contain one or more heteroatoms and are optionally interrupted by a heteromacrocycle, at least one of the radicals (A), (B) and (C) also containing at least one molecular moiety or essentially consisting of a molecular moiety, said molecular moiety possessing a greater triplet energy than that of the emission level of the completed rare earth ion.

9. A conjugate according to claim 8, wherein the fluorescent marker is a rare earth cryptate of formula (I) in which the molecular moiety is selected from the group consisting of phenanthroline, anthracene, benzene, naphthalene, bi- and terphenyl, azobenzene, azopyridine, pyridine, bipyridines, bis-quinolines and the compounds of the following formulae:

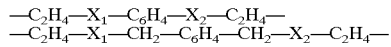

in which $X_1$ and $X_2$, which can be identical or different, are oxygen, nitrogen or sulfur, and

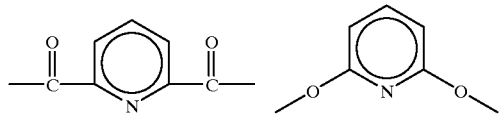

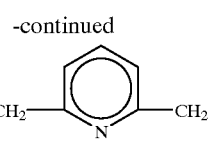

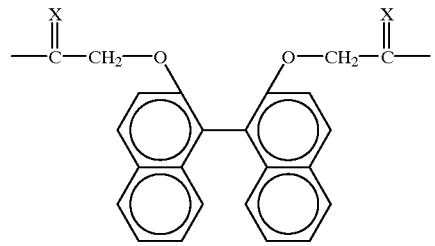

in which X is oxygen or hydrogen.

10. A conjugate according to claim 8, wherein the fluorescent marker is a rare earth cryptate consisting of a terbium or europium ion complexed by a macrocyclic compound selected from the group consisting of:

[2.2.phenanthroline]; [2.2.phenanthroline amide];

[2.2.anthracene]; [2.2.anthracene amide];

[2.2.biisoquinoline]; [2.2.biphenyl-bis-pyridine];

[2.2.bipyridine]; [2.2.bipyridine amide]; and tris-bipyridine, tris-phenanthroline, phenanthroline-bisbipyridine, biisoquinoline-bis-bipyridine and bis-bipyridine diphenylbipyridine macropolycycles.

11. A conjugate according to claim 10, wherein the fluorescent marker is the europium cryptate Eu tris-bipyridine.

12. A conjugate according to claim 1, wherein the fluorescent marker is a rare earth cryptate consisting of at least one rare earth salt complexed by a macropolycyclic compound comprising a molecular moiety selected from the group consisting of bipyrazines, bipyrimidines and nitrogen heterocycles containing N-oxide groups.

13. A conjugate according to claim 1, wherein the fluorescent marker is a rare earth cryptate consisting of at least one rare earth salt complexed by a macropolycyclic compound of formula II or III below:

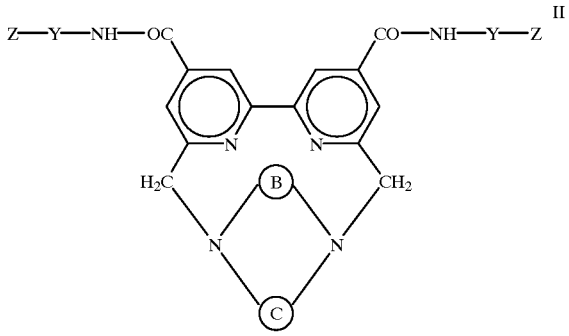

II

-continued

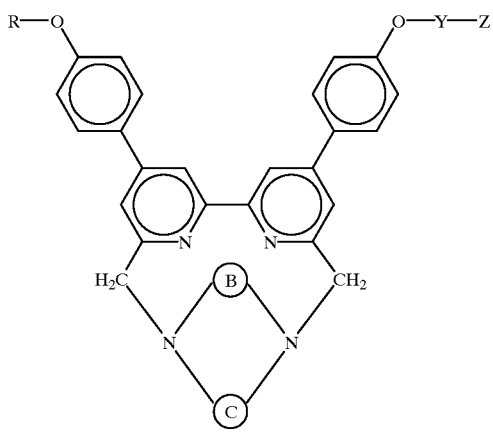

in which:
the ring of the formula

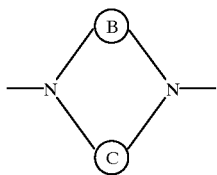

is one of the following rings:

1)

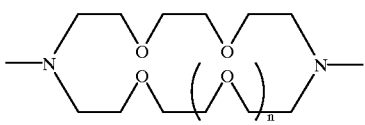

n = 0 or 1
[N₂O₄] macrocycle or (2.2) ring
[N₂O₃] macrocycle or (2.1) ring or

2)

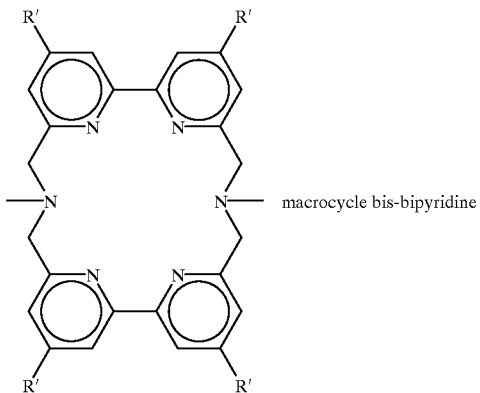

macrocycle bis-bipyridine

Y is a group or spacer arm consisting of a divalent organic radical selected from linear or branched $C_1$, to $C_{20}$ alkylene groups optionally containing one or more double bonds and/or optionally containing one or more heteroatoms such as oxygen, nitrogen, sulfur or phosphorus, or one or more carbamoyl or carboxamido groups, from $C_5$ to $C_8$ cycloalkylene groups or from $C_6$ to $C_{14}$ arylene groups, said alkylene, cycloalkylene or arylene groups optionally being substituted by alkyl, aryl or sulfonate groups;

Z is a functional group capable of bonding covalently with a biological substance;

R is a methyl group or the group —Y—Z; and

R' is hydrogen or a group —COOR", in which R" is a $C_1$ to $C_{10}$ alkyl group, or R' is a group —CO—NH—Y—Z.

14. A conjugate according to claim 1, wherein the fluorescent marker is bonded to the ribo- or deoxyribo-nucleoside or -nucleotide via a spacer arm consisting of a divalent organic radical selected from linear or branched $C_1$–$C_{20}$ alkylene groups optionally containing one or more double bonds or triple bonds and/or optionally containing one or more heteroatoms selected from the group consisting of oxygen, nitrogen, sulfur and phosphorus, or one or more carbamoyl or carboxamido groups; $C_5$–$C_8$ cycloalkylene groups; and $C_6$–$C_{14}$ arylene groups, said alkylene, cycloalkylene or arylene groups optionally being substituted by alkyl, aryl or sulfonate groups.

15. A conjugate according to claim 14, wherein the spacer arm is selected from the following groups:

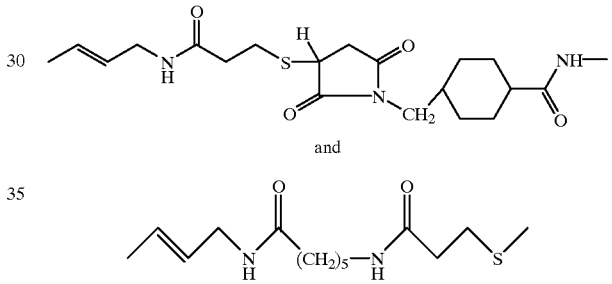

and

16. A conjugate according to claim 6, wherein the deoxyribonucleotide is deoxyuridine, the fluorescent marker is the europium cryptate Eu tris-bipyridine and the spacer arm is a 3-aminoalkyl group.

17. A process for preparing the conjugate according to claim 1, wherein a ribo- or deoxyribo-nucleoside or -nucleotide which is native, chemically modified or conjugated with one or more labeling molecules, in which at least one carbon atom of the ring or exocyclic nitrogen atom of the purine or pyrimidine ring or else carbon atom of the pentofuranose unit is able to bond with a fluorescent marker, is reacted with at least one fluorescent marker consisting of a rare earth cryptate bonded to said atom(s).

18. A polynucleotide comprising more than one conjugate according to claim 8.

19. A method of measuring the activity of an enzyme involved in a nucleic acid synthesis reaction, comprising
preparing a fluorescent conjugate of a nucleoside or nucleotide, comprising:
a ribo- or deoxyribo-nucleoside or -nucleotide which is native, chemically modified or conjugated with one or more labeling molecules, in which either
(a) at least one carbon atom of the ring or exocyclic nitrogen atom of the purine or pyrimidine ring or of the carbon atom of the pentofuranose unit is able to bond with a fluorescent marker; or (b) at least one carbon atom of the ring or exocyclic nitrogen atom of the purine or pyrimidine ring is able to bond with a fluorescent marker; and at least one fluorescent marker consisting of a rare earth cryptate bonded to said atom(s);

carrying out the nucleic acid synthesis reaction using said conjugate as a constituent nucleotide in the reaction; and measuring fluorescence emitted directly or indirectly by the conjugate;

wherein the enzymatic activity is indicated by the amount of fluorescence emitted.

20. A method according to claim 9, wherein the enzyme is selected from the group consisting of DNA or RNA polymerase, reverse transcriptase, transferase and ligase.

21. A method according to claim 19, comprising measuring enzymatic activity in the presence of a nucleic acid substrate.

22. A conjugate according to claim 13, wherein R" is selected from the group consisting of methyl, ethyl and tert-butyl.

* * * * *